US008543415B2

(12) United States Patent
Venon et al.

(10) Patent No.: US 8,543,415 B2
(45) Date of Patent: Sep. 24, 2013

(54) MOBILE MEDICAL DEVICE IMAGE AND SERIES NAVIGATION

(75) Inventors: Medhi Venon, Whitefish Bay, WI (US); Sukhdeep Gill, London (CA); Christopher Janicki, Sleepy Hollow, IL (US)

(73) Assignee: General Electric Company, Schenectady, NY (US)

( * ) Notice: Subject to any disclaimer, the term of this patent is extended or adjusted under 35 U.S.C. 154(b) by 652 days.

(21) Appl. No.: 12/324,627

(22) Filed: Nov. 26, 2008

(65) Prior Publication Data

US 2010/0131294 A1 May 27, 2010

(51) Int. Cl.
*G06Q 10/00* (2012.01)
*G06Q 50/00* (2012.01)

(52) U.S. Cl.
USPC .................................................. 705/2; 705/3

(58) Field of Classification Search
USPC ........................................................ 705/2, 3
See application file for complete search history.

(56) References Cited

U.S. PATENT DOCUMENTS

| 7,864,163 | B2* | 1/2011 | Ording et al. ................. 345/173 |
|---|---|---|---|
| 2001/0051881 | A1* | 12/2001 | Filler ................................. 705/3 |
| 2002/0184325 | A1* | 12/2002 | Killcommons et al. ...... 709/206 |
| 2003/0055686 | A1* | 3/2003 | Satoh et al. ........................ 705/3 |
| 2005/0114788 | A1* | 5/2005 | Fabritius ........................ 715/767 |
| 2006/0017692 | A1* | 1/2006 | Wehrenberg et al. .......... 345/156 |
| 2007/0078674 | A1* | 4/2007 | Weinberg et al. ................. 705/1 |
| 2008/0119237 | A1* | 5/2008 | Kim ................................. 455/566 |
| 2009/0138800 | A1* | 5/2009 | Anderson et al. ............. 715/702 |
| 2010/0198608 | A1* | 8/2010 | Kaboff et al. ..................... 705/2 |

\* cited by examiner

*Primary Examiner* — Neha Patel
(74) *Attorney, Agent, or Firm* — Hanley, Flight and Zimmerman, LLC

(57) ABSTRACT

Certain embodiments of the present invention provide systems and methods for mobile access to clinical information. Certain embodiments provide a mobile medical computing device system. The system includes a mobile medical computing device providing for display of, interaction with, and manipulation of medical images and patient data, the mobile medical computing device in communication with a clinical information system to exchange clinical content related to the medical images and patient data.

10 Claims, 13 Drawing Sheets

MOBILE MEDICAL DEVICE IMAGE AND SERIES NAVIGATION

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

Healthcare environments, such as hospitals or clinics, include information systems, such as hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR). Information stored may include patient medical histories, imaging data, test results, diagnosis information, management information, and/or scheduling information, for example. The information may be centrally stored or divided at a plurality of locations. Healthcare practitioners may desire to access patient information or other information at various points in a healthcare workflow. For example, during and/or after surgery, medical personnel may access patient information, such as images of a patient's anatomy, that are stored in a medical information system. Radiologist and/or other clinicians may review stored images and/or other information, for example.

Using a PACS and/or other workstation, a clinician, such as a radiologist, may perform a variety of activities, such as an image reading, to facilitate a clinical workflow. A reading, such as a radiology or cardiology procedure reading, is a process of a healthcare practitioner, such as a radiologist or a cardiologist, viewing digital images of a patient. The practitioner performs a diagnosis based on a content of the diagnostic images and reports on results electronically (e.g., using dictation or otherwise) or on paper. The practitioner, such as a radiologist or cardiologist, typically uses other tools to perform diagnosis. Some examples of other tools are prior and related prior (historical) exams and their results, laboratory exams (such as blood work), allergies, pathology results, medication, alerts, document images, and other tools. For example, a radiologist or cardiologist typically looks into other systems such as laboratory information, electronic medical records, and healthcare information when reading examination results.

PACS were initially used as an information infrastructure supporting storage, distribution, and diagnostic reading of images acquired in the course of medical examinations. As PACS developed and became capable of accommodating vast volumes of information and its secure access, PACS began to expand into the information-oriented business and professional areas of diagnostic and general healthcare enterprises. For various reasons, including but not limited to a natural tendency of having one information technology (IT) department, one server room, and one data archive/backup for all departments in healthcare enterprise, as well as one desktop workstation used for all business day activities of any healthcare professional, PACS is considered as a platform for growing into a general IT solution for the majority of IT oriented services of healthcare enterprises.

BRIEF SUMMARY OF THE INVENTION

Certain embodiments of the present invention provide systems and methods for mobile access to clinical information.

Certain embodiments provide a mobile medical computing device system. The system includes a mobile medical computing device providing for display of, interaction with, and manipulation of medical images and patient data, the mobile medical computing device in communication with a clinical information system to exchange clinical content related to the medical images and patient data.

Certain embodiments provide a mobile medical device. The device includes a user interface for display of and interaction with medical content retrieved from one or more clinical systems, wherein a user can manipulate content, access different content, and collaborate with other users to analyze and report on exams and other medical content. The mobile medical device includes a plurality of modes, wherein a change in device orientation results in a change in device mode and set of available tools without closing or losing a patient context and one or more previous screens of patient information.

In certain embodiments, enterprise functionality and real-time collaboration are provided for a user to collaborate on a document in real time with other users and access and change content from one or more clinical systems.

In certain embodiments, the device includes an accelerometer detecting motion of the device and allowing a user to navigate through different screens of patient content and functionality based on the detected motion.

Certain embodiments provide a method for clinical image and information review and manipulation via a mobile medical device. The method includes providing a user interface for display of and interaction with medical content retrieved from one or more clinical systems, wherein a user can manipulate content, access different content, and collaborate with other users to analyze and report on exams and other medical content. The method also includes selecting a mode for the mobile medical device from a plurality of modes, wherein a change in device orientation results in a change in device mode and set of available tools without closing or losing a patient context and one or more previous screens of patient information.

Figure 1:
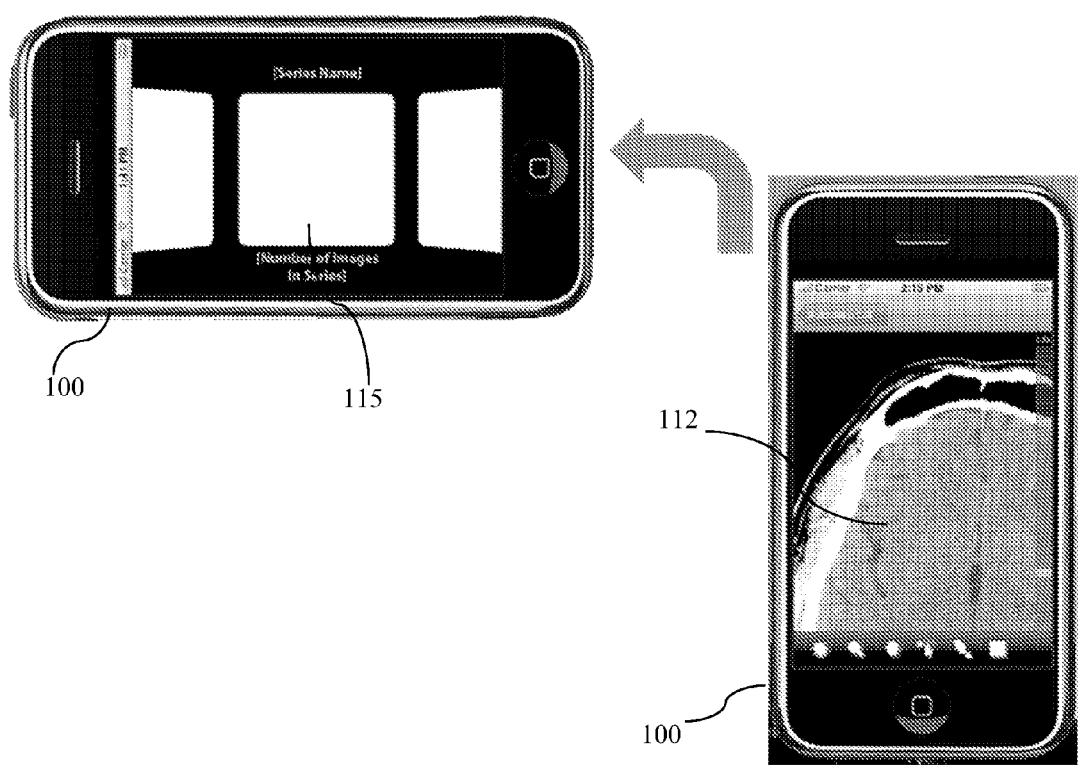
FIG. 1 illustrates a mobile medical device allowing a user to switch between navigation and image viewing modes without user interface input in accordance with certain embodiments of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF CERTAIN EMBODIMENTS

Certain embodiments provide a mobile medical device offering comprehensive healthcare information technology services on a mobile computing device platform. Certain embodiments leverage configuration and flexibility capabilities of a mobile device to provide workflow enhancement and usability advantages to healthcare practitioners.

The mobile medical device allows a user to display and interact with medical content stored on one or more clinical systems via the mobile handheld device. Without user interaction via a pointing device or button selection, a user can manipulate content, access different content, and collaborate with other users to analyze and report on exams and other medical content. A change in device orientation results in a change in device mode and set of available tools without closing or losing the patient context and previous screen(s) of patient information. Images can be manipulated, annotated, highlighted, and measured via the device. Enterprise functionality and real-time collaboration are provided such that the user can collaborate on a document in real time with other users as well as access content from systems such as a RIS, PACS, etc., and make changes via the mobile device.

The mobile medical device displays and interacts with medical content via a plurality of modes. Each mode includes different content and associated tools. Each of the plurality of modes is accessible based on a change in orientation and/or position of the device while maintaining a patient context across modes. The mobile device also includes medical content analysis capability for display, manipulation, and annotation of medical content and real-time sharing of the content for user collaboration using multi-touch control by the user. The mobile device communicates with one or more clinical systems to access and modify information from the one or more clinical systems in substantially real-time.

Certain embodiments provide a mobile medical device for displaying and interacting with medical content. The mobile medical device facilitates user workflow. For example, the mobile medical device uses an accelerometer and/or other positional/motion indicator to allow a user to navigate through different screens of patient content and functionality without losing or closing a previous screen. A user can navigate through an exam's content over multiple worklist items without going back to the worklist. The mobile medical device removes the requirement of using a user interface control to select between different screens. For example, multi-touch capability is provided to manipulate and modify content. Using multi-touch, a user can draw shapes and annotate to generate measurements, highlight abnormal structure, and/or add textual comments to an image, for example. Via the mobile medical device, a user can input and/or manipulate without adding external input devices.

In certain embodiments, the mobile medical device provides enhance resetability for the user. For example, the device can undo, erase, and/or reset end user changes to default setting by tracking a device's position and/or orientation and responding to changes to the position/orientation. The device can undo and restart without additional user interface control input. The device can adjust a threshold parameter through user feedback, for example (e.g., a current setting may be too sensitive to normal movement of the device when carried or held by a user).

Certain embodiments integrate enterprise functions into a mobile medical device. For example, functionality such as a directory, calendar, geographic location, phone services, text message, email, etc., can be provided via the mobile medical device. Clinical information from various sources such as PACS, HIS, RIS, etc., can be provided via the mobile medical device. The mobile medical device interface can facilitate real-time collaboration with other end users. Information sharing and recording can be facilitated using multiple media services in real-time or substantially real-time, for example. The mobile medical device allows the user to focus on patient information and analysis while collaborating with one or more end users without switching or leaving the clinical context being reviewed, as well as exchanging medical data without losing the current state of the clinical context, for example. The mobile medical device provides a unified communication/collaboration point that can query and access information throughout different information systems, for example.

Certain embodiments facilitate user authentication via the mobile medical device. For example, the mobile medical device can authenticate a user's access to sensitive and/or private information. In certain embodiments, user authentication at the mobile medical device does not require the user to enter an identifier and password. Instead, the user is known, and the mobile device verifies if the current user is authorized for the particular content/application. Authentication is based on a unique identification number for the device, a connectivity parameter, and a PIN number for the user to enter, for example.

FIG. 1 illustrates a mobile medical device 100 allowing a user to switch between navigation and image viewing modes without user interface input in accordance with certain embodiments of the present invention. The mobile medical device 100 can be turned to landscape mode 110 (e.g., turned left) to switch from a single image view 112 to view and select an image series 115. The device 100 screen surface is kept clear with little textual information other than a name of the image series and a number of images in the currently viewed series, for example.

Figure 2:
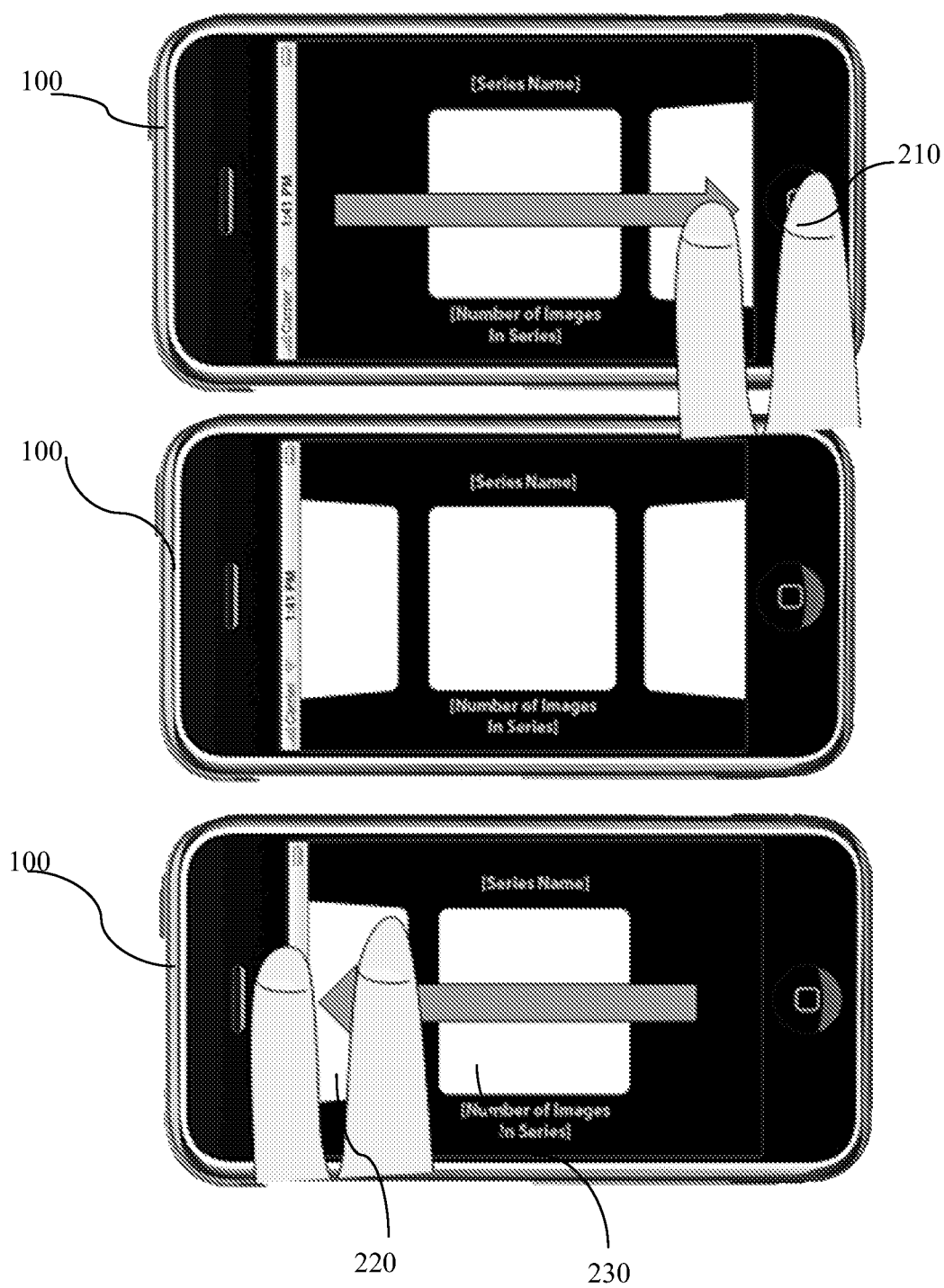
FIG. 2 illustrates a mobile medical device facilitating image navigation in accordance with certain embodiments of the present invention.

FIG. 2 illustrates a mobile medical device 100 facilitating image navigation in accordance with certain embodiments of the present invention. For example, the device 100 allows navigation of an image series using a finger swipe gesture 210. A user can swipe right to increment a selected index by one, for example. A user can swipe left to decrement a selected index by one, for example. Additional series available for view are indicated by an angled series thumbnail 220 on left or right of the centered series thumbnail image 230.

Figure 3:
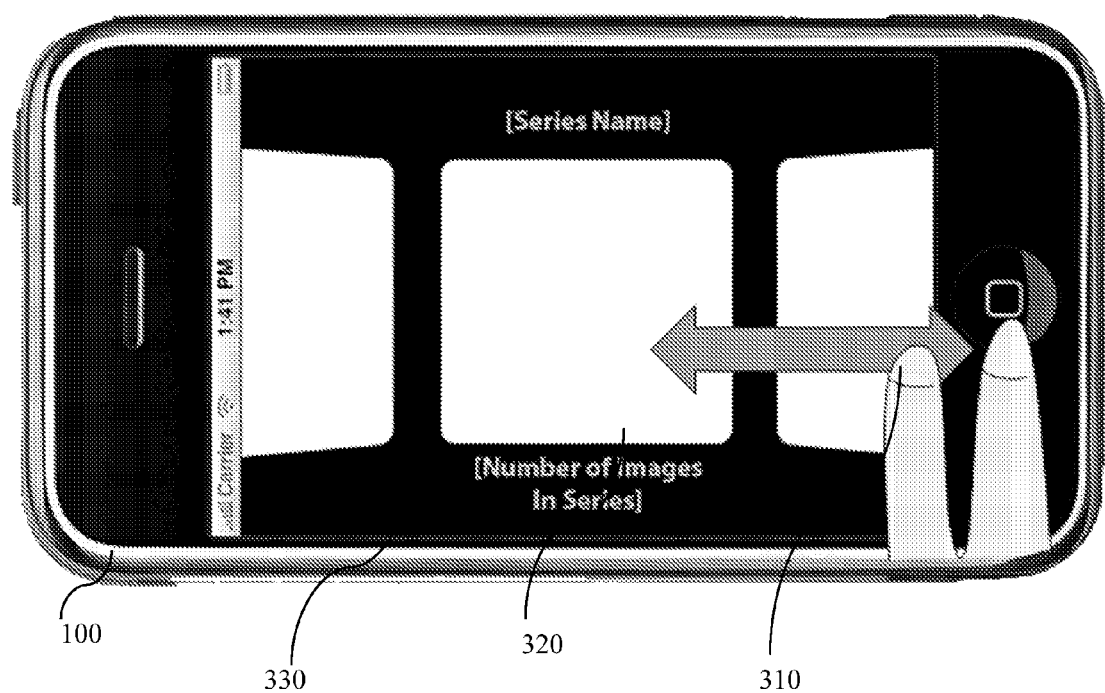
FIG. 3 illustrates image display and preview within a series using a mobile medical device.

As illustrated in FIG. 3, images within a series can be previewed by skimming a single finger across a series thumbnail image 310. The location of a user's finger divided by an image series thumbnail width equals image index divided by a total number of images in the series. Rotating the mobile medical device 100 back to portrait mode will set the current image 320 in the image viewer 330 to the image index of on the series thumbnail.

Figure 4:
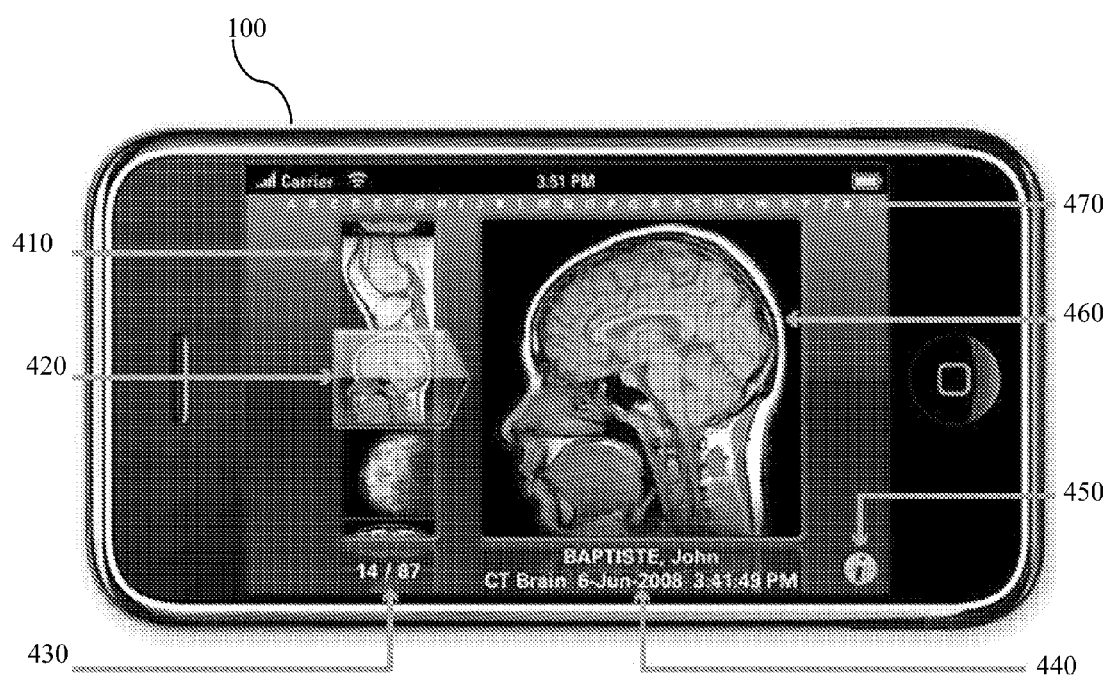
FIG. 4 shows a mobile medical device providing an image series browser that allows a user to skim vertically in order to slide image series thumbnails past a selector.

As shown in FIG. 4, a mobile medical device 100 can provide an image series browser 410 that allows a user to skim vertically in order to slide image series thumbnails past a selector. A selected series indicator 420 allows an image series to be selected by sliding a thumbnail image below the indicator. The series thumbnails "snap" into position to facilitate easier selection. A series counter 430 indicates a selected series and a total number of series, for example. Series information 440 provides information including patient name, procedure, and procedure date, for example. A information/settings button 450 allows a user to display available display settings upon a tap of the button. A series image viewer 460 allows a user to skim horizontally to cine through images in the series. Skimming over an alphabetical index 470 advances the thumbnail picker 420 to that point in the alphabet based on the patient's name. Using the picker control, when a thumbnail image appears within the selector 420, the images in that series are displayed to the right, along with the patient's name, the procedure, and the procedure date, for example.

Figure 5:
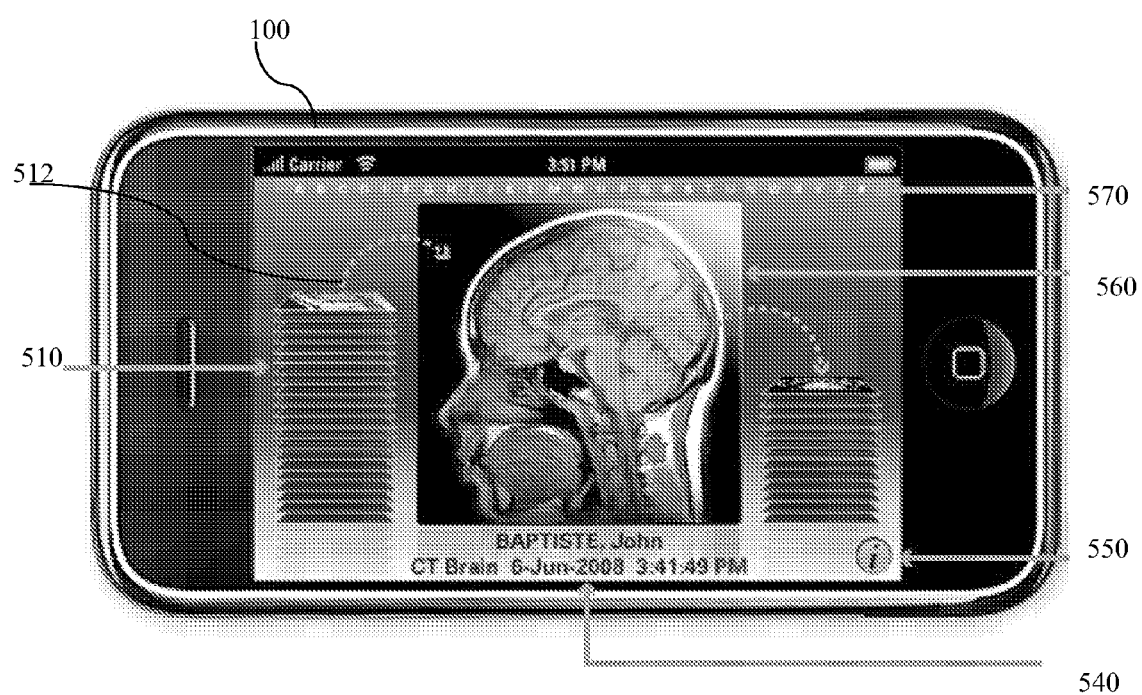
FIG. 5 depicts a mobile medical device using a representation of a film or image stack to provide a visual indicator for a total number of series and an intuitive interface for navigating through the series.

In FIG. 5, a mobile medical device 100 uses a representation of a film or image stack to provide a visual indicator for a total number of series and an intuitive interface for navigating through the series. The device 100 provides a film stack 510 from which series are selected by sliding a thumbnail 512 from the stack on the left to the series image viewer 560. Series information 540 provides information including patient name, procedure, and procedure date, for example. A information/settings button 550 allows a user to display available display settings upon a tap of the button. A series image viewer 560 allows a user to skim horizontally to cine through images in the series. Skimming over an alphabetical index 570 advances a thumbnail picker in the stack 510 to that point in the alphabet based on the patient's name.

Figure 6:
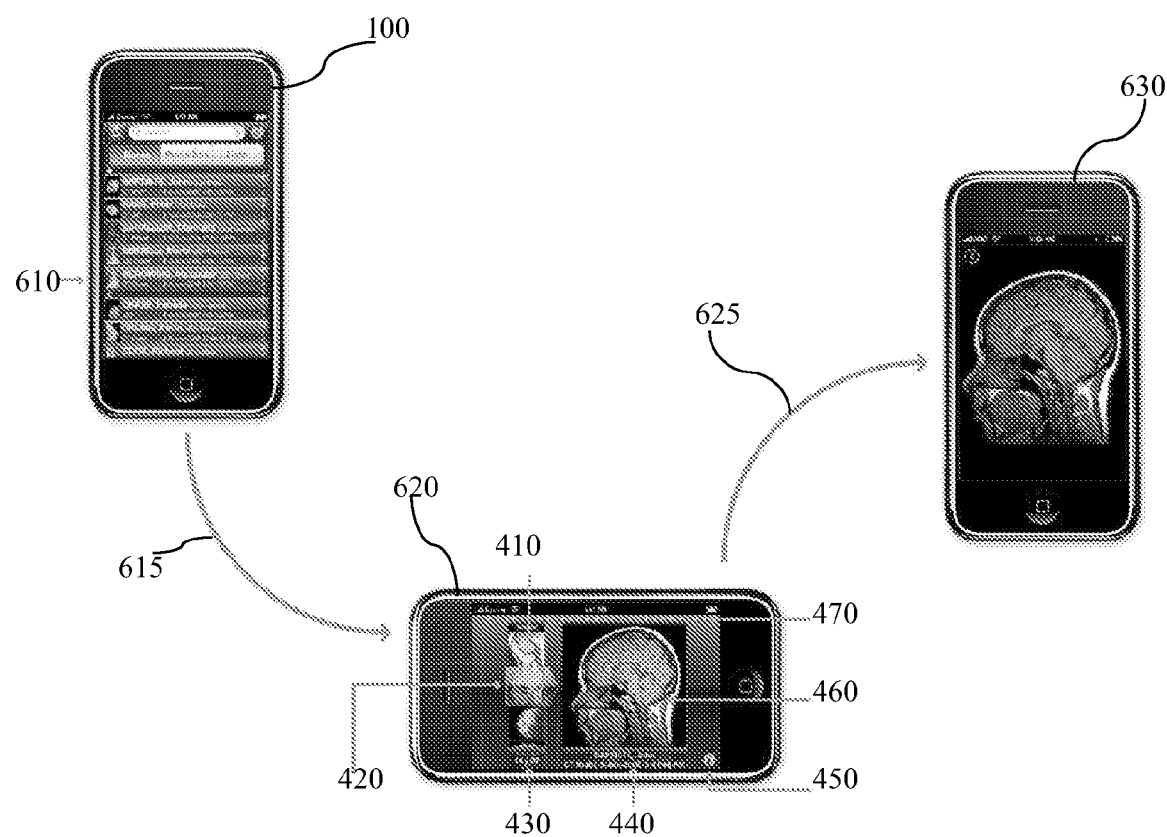
FIG. 6 illustrates a mobile medical device workflow in accordance with certain embodiments of the present invention.

FIG. 6 illustrates a mobile medical device 100 workflow in accordance with certain embodiments of the present invention. At 605, a worklist screen 610 allows a user to select a patient by tapping the display over the worklist item. At 615, turning the device 100 horizontally switches a mode of the device 100 to a series picker mode 620, such as the series picker mode described above with respect to FIG. 4. At 625, selecting a series and turning the device 100 vertically switches a mode of the device 100 to an image viewer mode 630.

Figure 7:
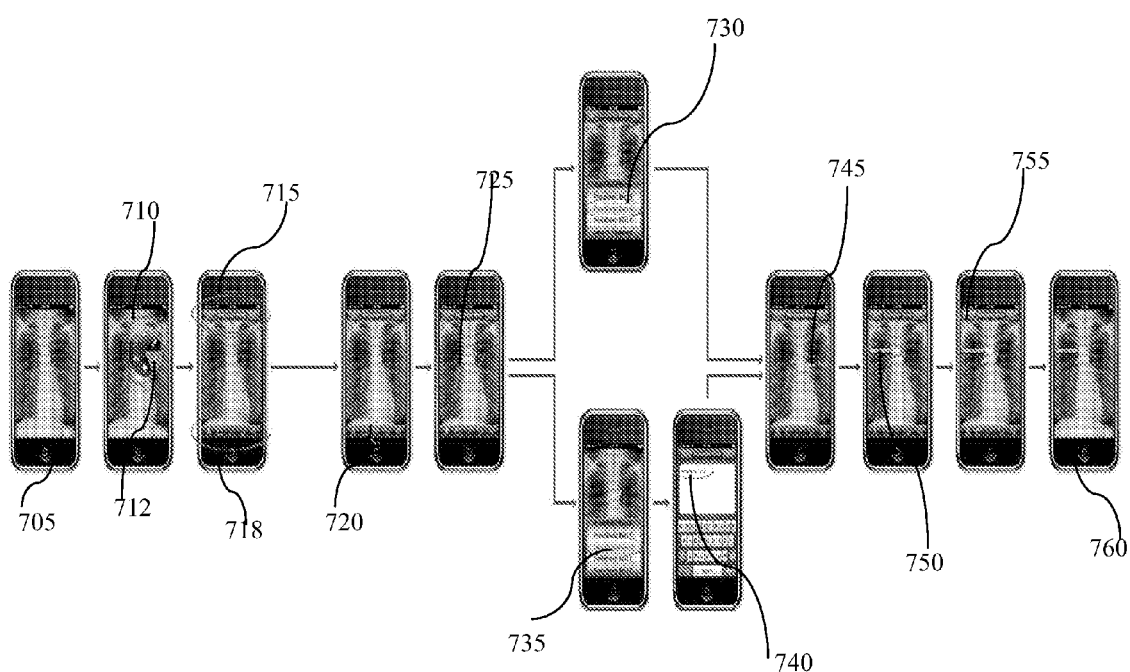
FIG. 7 depicts a mobile medical device presented in an image viewer mode.

As shown in FIG. 7, the mobile medical device 100 is presented in an image viewer mode 705. A user taps to launch a pie menu 710, from which he or she selected an annotation tool 712. Entering an annotation mode, a navigation bar 715 and a tool bar 718 are activated. The toolbar 718 contains various annotation tools. The navigation bar 715 allows the user to clear or save the annotations. A user can tap or otherwise select an appropriate annotation tool 720 from the toolbar 718. The user can then define an area of interest 725 on the image. Once the area of interest 725 is defined, the picker 730, containing predefined annotation text, appears. The user scrolls through the text choices and selects an appropriate annotation. Once the area of interest 725 is defined, the picker 730 appears including predefined annotation text. Once of the picker 730 choices is to launch keyboard 735. The user selects this option to enter custom annotation text. The user enters their annotation text via the keyboard 740. The viewer button closes the keyboard and returns to the image viewer (which is still in annotation mode). The clear button clears the annotation text.

When the user returns to the image viewer, the annotation text 745 appears near the area of interest. The user can drag the text to a different position 750. The user can then enter additional annotations to the image by repeating previous steps. Tapping and/or otherwise selecting a save button 755 saves the annotation text, exits annotation mode, and returns to the image viewer. At 760, the annotation is saved with the image.

Using the annotation tools, the user can draw shapes (e.g., square, rectangle, ellipse, circle, polygon, etc.) and annotate measurements (e.g., angle, length, volume, etc.). These functions can be used during image viewing to generate measurements, highlight abnormal structure in the anatomy, and/or add textual comments related to the image, for example. A single or multi-touch input from the user allows a single and/or concurrent touch to define line endpoints, origin and size of a rectangle, origin and size of a circle, drawing free form shapes, etc. Textual data can be added by a combination of preset text data and an electronic keyboard for custom txt.

In certain embodiments, a motion pattern of the mobile device 100 acts as an erase or reset pattern. Such motion can be used to undo, erase, or reset end user changes to a default presentation state for an exam's images, reports, non-image medical evidence, etc. An eraser motion pattern can be based on, but not limited to, a hardware component that tracks a device's position or orientation such as, but not limited to, an accelerometer sensor or geographic positioning sensor. Depending on the context, the gesture performed by the user could have a variety of effects. For example, shaking the device 100 one time could undo or reset based on user choice. Shaking the device 100 two times could reset the viewer to an original or default state. Shaking can be defined by a change in the spatial acceleration of the device during a certain time period (e.g., one second) and then repeats once (e.g., one time), for example. The device 100 detects a strong acceleration in an opposite direction, and two consecutive times define the shaking motion. Thus, two shakes indicates that the shake pattern should be repeated two times during a short time window. Parameter(s) to define the threshold of acceleration, the time window of each motion and the shaking sequence can be adjusted through user validation and user feedback, for example.

In certain embodiments, user authentication is facilitated at the mobile medical device 100 to protect access to sensitive information displayed by an application. Using the device 100, it is assumed that the user is known, and it is then verified whether the current user is an authorized user of the application. Authentication is based on the device's unique identification number, a connectivity parameter from the device to the application, and a PIN number for the user to enter, for example. Thus, a device to server/system authentication is performed by this process, and an end user to device authentication is done by a simple device-level authentication. A user is relieved from and/or is provided an alternative to presenting credentials to a device through traditional peripherals/devices; including but not limited to a keyboard, biometric authentication, etc.

Mobile devices (including but not limited to a smart phone, laptop, personal digital assistant, cellular phone, handheld computer (e.g., Blackberry or iPhone), etc) follow standards and protocols that mandate a description or identifier for the communicating component (including but not limited to a network device MAC address, a phone number, a GSM phone serial number, an International Mobile Equipment Identifier, and/or other device identifying feature). These identifiers can fulfill a security requirement for device authentication. The identifier is used in combination with a front-end user interface component that leverages a multi-touch input device such as but not limited to; Personal Identification Number, Keyword, Drawing/Writing a signature (including but not limited to; a textual drawing, drawing a symbol, drawing a pattern, performing a gesture, etc), etc., to provide a quick, natural, and intuitive method of authentication. Feedback can be provided to the user regarding successful/unsuccessful authentication through display of animation effects on a mobile device 100 user interface. For example, the device 100 can produce a shaking of the screen when user authentication fails. Security standards, virtual private network access, encryption, etc., can be used to maintain a secure connection.

Figure 8:
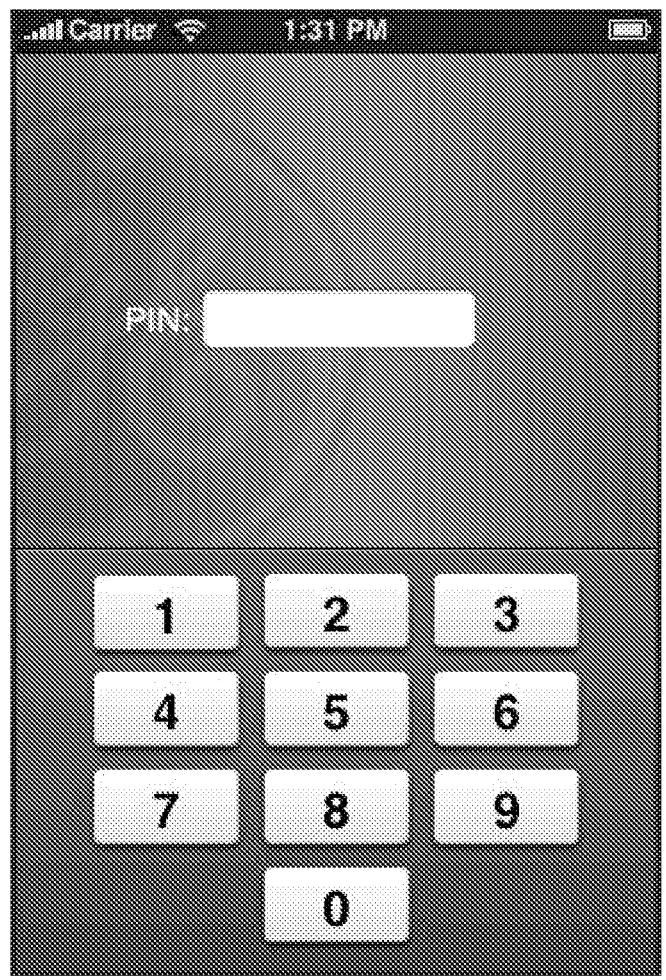
FIG. 8 depicts an example of PIN authentication on a mobile medical device.

For example, an end user launches a secure application (including but not limited to a clinical application requiring a degree of security). The application reads the unique identifying features of the device 100 and perform an authentication "hand-shake" with the server or data-providing system. This process is automated with no user input or interaction required. After the device has been authenticated, the user is presented with an application/user level authentication screen (including but not limited to a personal identification number ("PIN"), password/passcode, gesture, etc.) to identify to the application that the user is indeed a valid user. See, for example, the PIN authentication of FIG. 8. This feature functions as a method to provide device level security as well as an ability to lock the device (e.g., if the user wishes to temporary lock the device but not logout/shutdown the application), for example.

In certain embodiments, mobile devices, such as but not limited to smart phones, ultra mobile and compact notebook computers, personal digital assistants, etc., offer many applications aside from phone functions. Certain embodiments allow clinical end users to enhance their collaboration with their colleagues, patients, and hospital enterprise via the mobile device 100.

By integrating enterprise functions for mobile devices, such as but not limited to a directory, calendar, geographic location, phone services, text messages, email services, etc., with clinical information from various clinical sources, such as but not limited to PACS, HIS, RIS, etc., end users can access patient centric information and enable real-time or substantially real-time collaboration with other end users to collaborate on a specific patient case. The collaboration allows information sharing and recording using multiple media services in real-time or substantially real-time.

Collaboration leverages global positioning system, multi-touch capability, high resolution displays, etc., in mobile devices within small form factors, for example. Using the mobile medical device 100, the end user can focus on patient information analysis while collaborating with one or many other end users without switching or leaving the clinical context being reviewed. It allows exchanging medical data without losing the current state of the clinical context. It also leverages all the multi-media features of a device from healthcare applications. For example, clinical and non-clinical information can be provided to aid a clinical user, such as a physician, nurse, technologist, administrator, etc., in patient care and workflow decisions. The device 100 provides the user with an ability to locate and contact another user (including but not limited to a patient, referring physician, surgeon, pharmacy, emergency patient contact, etc.). The device 100 provides an ability to locate and provide directions with a map to an address of another user, department, or institution (including but not limited to a home address, business address, drug store, hospital clinic, hospital remote facility, specialized clinical facility, etc.). Using a contact address and current location determined by a built-in global positioning feature, a map and guide route can be generated to the destination. This feature also allows relatively accurate time estimates for travel to reach a destination. The device 100 provides an ability to locate and contact another user involved in a patient's care by navigating a user interface that provides contact information of other users involved in the patient's care. Communication is then initiated (including but not limited to by phone, SMS, text messaging, email services, etc.) to collaborate on a patient's exam/case/care. Other users can be included as needed by using the interface (including but not limited to a multi-touch user interface) to search through a contact list (including but not limited to a local contact list, enterprise contact list, clinical context contact list, etc.). Clinical information can then be conveyed to collaborators through a variety of communication methods (including but not limited to phone, SMS, text messaging, email services, etc.) and added to the patient's care record (including but not limited to Clinical Report, Audit Tracking, etc.). Navigation through this information is provided by a user interface that accepts multi-touch user input, for example.

Figure 9:
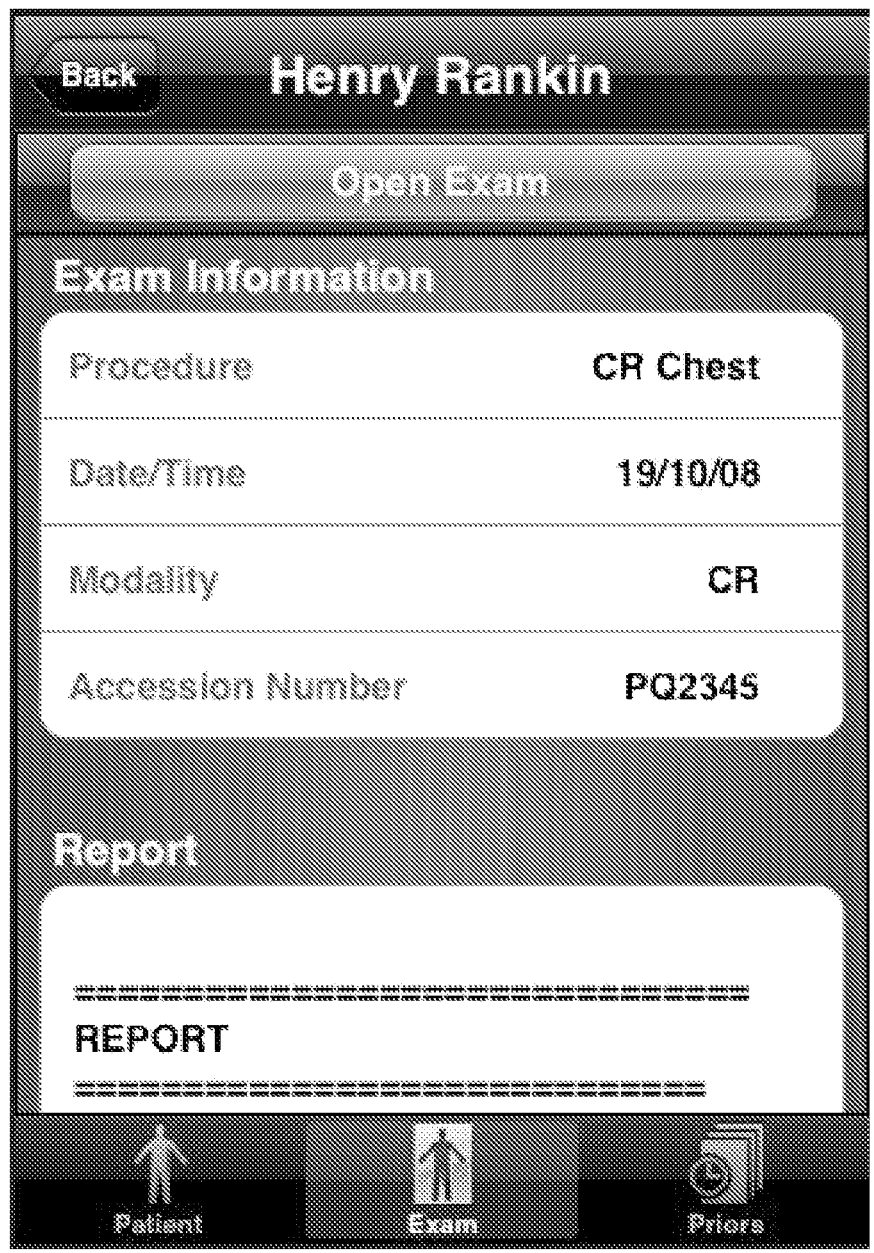
FIGS. 9-11 provide example contact information interfaces and displays in accordance with embodiments of the present invention.
Figure 10:
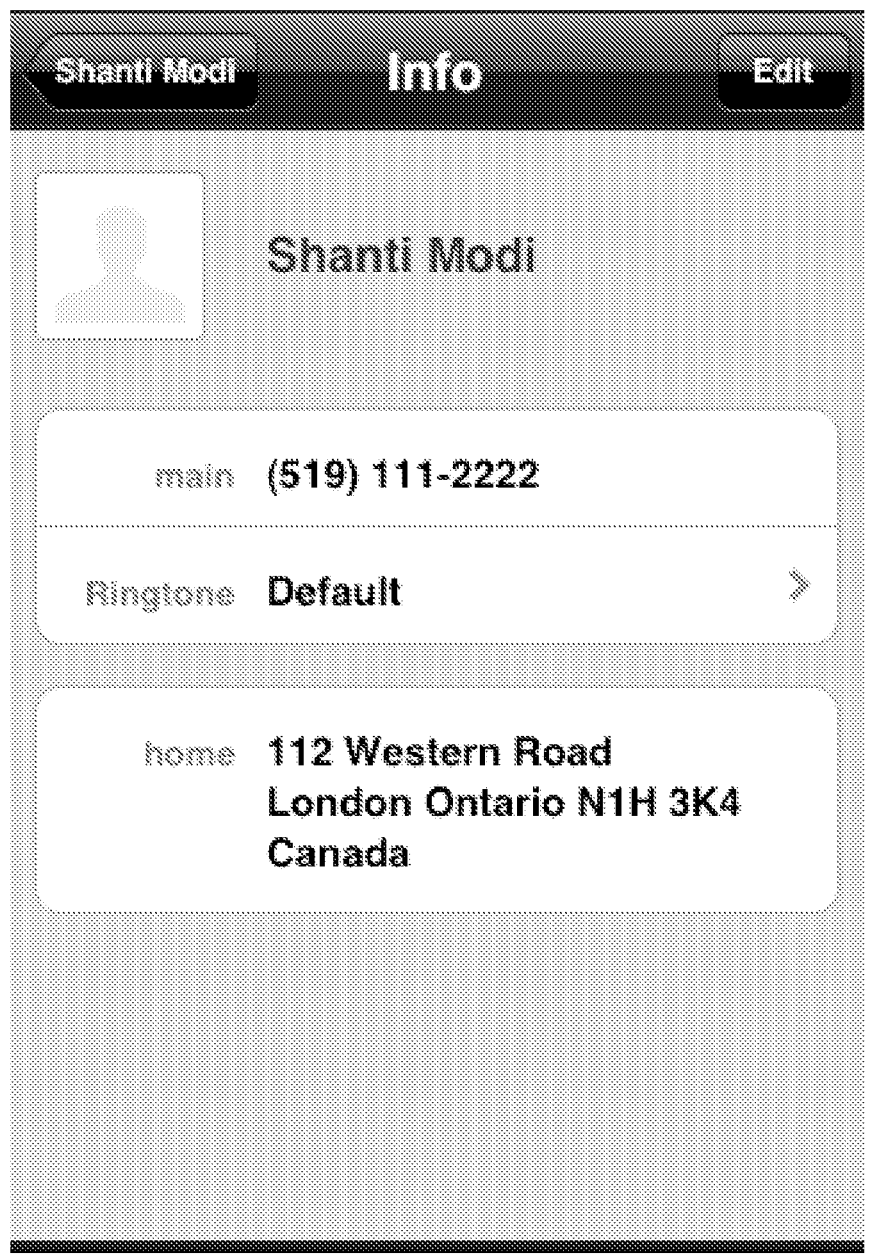
Figure 11:
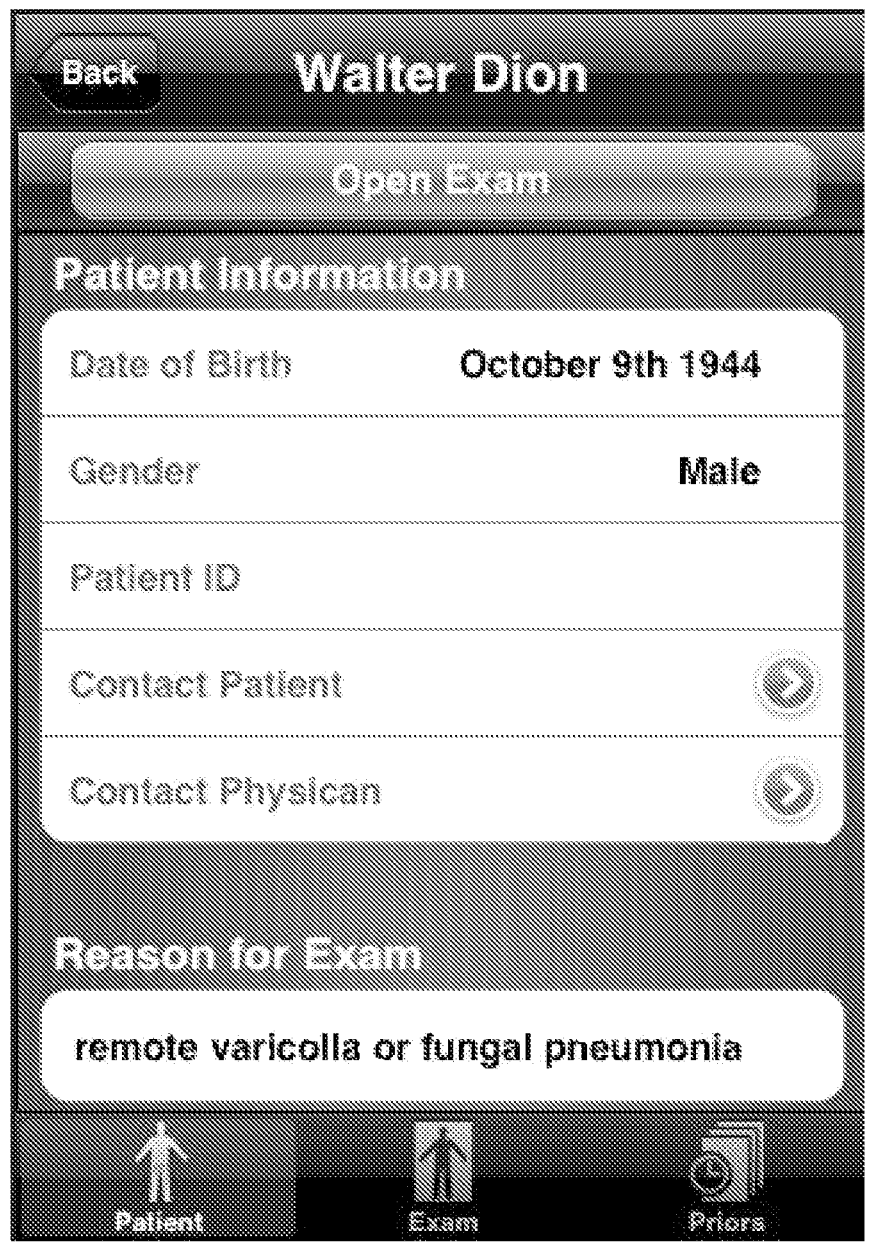

FIGS. 9-11 provide example contact information interfaces and displays in accordance with embodiments of the present invention.

Figure 12:
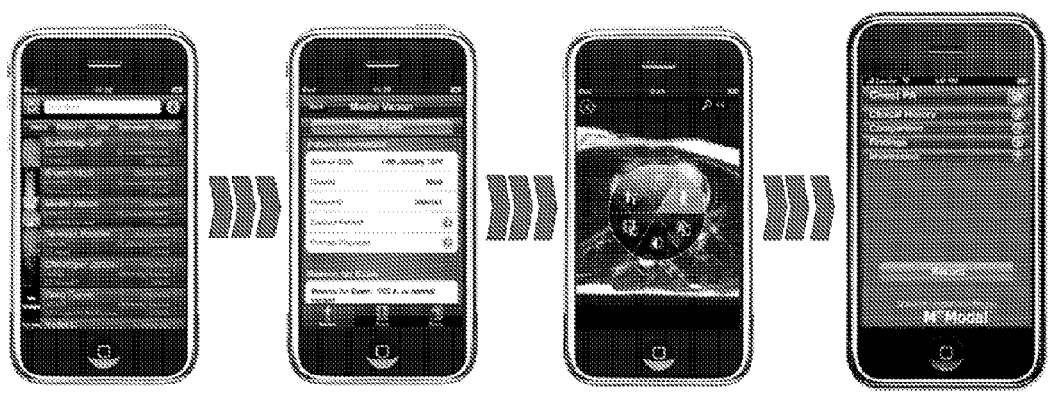
FIG. 12 provides a further example of mobile collaboration using a mobile medical device.
Figure 13:
FIG. 13 displays an example integration of dictated notes in an exam report section, emailing and/or other sharing of notes with a patient contact, image/exam annotation capabilities, etc. using a mobile medical device.

FIG. 12 provides a further example of mobile collaboration using a mobile medical device. Additionally, as reiterated in FIG. 13, certain embodiments provide integration of the dictated notes in an exam report section, emailing and/or other sharing of notes with a patient contact, image/exam annotation capabilities, etc.

Thus, certain embodiments provide mobile health solutions for a medical evidence workflow. Certain embodiments provide an intuitive key image annotation. Certain embodiments enable easy to use text annotation and reports for mobile radiology and/or other clinical solutions. Certain embodiments deliver a full enterprise radiology solution.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

One or more of the components of the systems and/or steps of the methods described above may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device. Certain embodiments of the present invention may omit one or more of the method steps and/or perform the steps in a different order than the order listed. For example, some steps may not be performed in certain embodiments of the present invention. As a further example, certain steps may be performed in a different temporal order, including simultaneously, than listed above.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of embodiments of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated computer-readable media provide nonvolatile storage of computer-executable instructions, data structures, program modules and other data for the computer.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A mobile medical computing device system, said system comprising:
    a mobile medical computing device comprising:
        a display configured to output content and accept user input;
        a processor;
        a sensor configured to detect motion of the device and enable a user to navigate through different screens of patient content and functionality based on the detected motion, wherein a certain sequence of device movement enables the user to at least one of undo, erase, and reset changes to a default device setting by tracking at least one of a position and orientation of the mobile medical device;
        a memory storing clinical content and machine-readable instructions for execution by said processor, wherein said clinical content comprises medical images and patient data;
        said processor configured to provide display of, interaction with, and manipulation of said medical images and patient data, the mobile medical computing device in communication with a clinical information system to exchange said clinical content related to the medical images and patient data,
        said processor configured to implement a user interface in conjunction with the display to display and interact with said clinical content retrieved from one or more clinical systems,
        wherein the user interface enables the user to manipulate said clinical content, access different content, and collaborate with other users to analyze and report on medical exams and other medical content,
        the mobile medical device including a plurality of modes, wherein each device mode includes different clinical content and associated tools, and wherein a change in device orientation results in a change in device mode and set of available tools without closing or losing a patient context and one or more previous screens of patient information,
        the mobile medical device configured to manipulate, annotated, highlight and measure the medical images; and
        the mobile medical device further configured to provide enterprise functions to enable the user to collaborate in real time with one or more other users and access and change content from the one or more clinical systems without switching or leaving a context being reviewed.

2. The mobile medical device of claim 1, wherein the mobile medical device is configured to enable user navigation through an exam's content over multiple worklist items without going back to the worklist.

3. The mobile medical device of claim 1, further comprising multi-touch interface recognition.

4. The mobile medical device of claim 3, wherein multi-touch capability is provided to manipulate and modify content.

5. The mobile medical device of claim 4, wherein said multi-touch capability enables the user to draw shapes and annotate to generate measurements, highlight abnormal structure, and add textual comments to an image.

6. The mobile medical device of claim 1, wherein the enterprise functions enable users to exchange medical data without losing a current state of the clinical context.

7. The mobile medical device of claim 1, wherein the device provides a unified communication point for querying and accessing information from a plurality of clinical information systems.

8. The mobile medical device of claim 1, wherein user authentication is facilitated at the mobile medical device based device identification information and entry of a personal identification number by the user.

9. A method for clinical image and information review and manipulation via a mobile medical device, said method comprising:

providing, by a processor in a mobile medical device, a user interface for display of and interaction with medical content retrieved from one or more clinical systems, wherein the user interface enables a user to a) manipulate the medical content, the content including medical images and patient data, b) access different content, and c) collaborate with other users to analyze and report on exams and other medical content;

detecting a motion of the device and enabling, by the processor, the user to navigate through different screens of patient content and functionality based on the detected motion, wherein a certain sequence of device movement enables the user to at least one of undo, erase, and reset changes to a default device setting by tracking at least one of a position and orientation of the mobile medical device; and selecting, based on the detected motion of the device, a mode for the mobile medical device from a plurality of modes, wherein each device mode includes different clinical content and associated tools, and wherein a change in device orientation results in a change in device mode and set of available tools without closing or losing a patient context and one or more previous screens of patient information, wherein the mobile medical device is configured to manipulate, annotate, highlight and measure the medical images, and wherein the mobile medical device is further configured to provide enterprise functions to enable the user to collaborate in real time with one or more other users and access and change content from the one or more clinical systems without switching or leaving a context being reviewed.

10. The method of claim 9, further comprising accepting multi-touch user input to draw shapes and annotate to generate measurements, highlight abnormal structure, and add textual comments to an image.

* * * * *